US006778846B1

(12) United States Patent
Martinez et al.

(10) Patent No.: US 6,778,846 B1
(45) Date of Patent: Aug. 17, 2004

(54) METHOD OF GUIDING A MEDICAL DEVICE AND SYSTEM REGARDING SAME

(75) Inventors: Gonzalo Martinez, Mendota Heights, MN (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/539,427

(22) Filed: Mar. 30, 2000

(51) Int. Cl.[7] ............................................... A61B 5/00
(52) U.S. Cl. ..................... 600/407; 600/427; 600/476
(58) Field of Search .......................... 606/130; 600/151, 600/407, 425, 429, 473, 427, 476

(56) References Cited

U.S. PATENT DOCUMENTS

| | | | | |
|---|---|---|---|---|
| 4,817,613 A | | 4/1989 | Jaraczewski et al. | 128/658 |
| 5,188,111 A | * | 2/1993 | Yates et al. | 128/657 |
| 5,396,902 A | | 3/1995 | Brennen et al. | 128/772 |
| 5,400,771 A | * | 3/1995 | Pirak et al. | 128/6 |
| 5,441,053 A | * | 8/1995 | Lodder et al. | 600/473 |
| 5,487,757 A | | 1/1996 | Truckai et al. | 607/122 |
| 5,520,178 A | | 5/1996 | Dahn et al. | |
| 5,645,520 A | * | 7/1997 | Nakamura et al. | 600/151 |
| 5,906,578 A | | 5/1999 | Rajan et al. | |
| 6,016,439 A | | 1/2000 | Acker | |
| 6,226,546 B1 | * | 5/2001 | Evans | 600/424 |
| 6,228,089 B1 | * | 5/2001 | Wahrburg | 606/86 |

FOREIGN PATENT DOCUMENTS

WO     WO 97/44089     5/1997

OTHER PUBLICATIONS

Skoog, et al., *Principles of Instrumental Analysis*, Fourth Edition, Harcourt Brace College Publishers, Copyright 1992 by Saunders College Publishing, pp. 69 and 296–308.

* cited by examiner

*Primary Examiner*—Ruth S. Smith
(74) *Attorney, Agent, or Firm*—Girma Wolde-Michael; Michael C. Soldner; Paul H. McDowall

(57) ABSTRACT

A method and system to guide a medical device within a patient using image data, e.g., chemical image data, includes acquiring image data of a view region within the patient. A movable element of the medical device is guided, e.g., self-guided, based on the image data. For example, the image data may be analyzed to detect a target area within the view region, e.g., the target area having at least one characteristic that is different from other portions within the view region. The movable element may then be guided based on the detected target area.

12 Claims, 5 Drawing Sheets

METHOD OF GUIDING A MEDICAL DEVICE AND SYSTEM REGARDING SAME

FIELD OF THE INVENTION

The present invention relates generally to medical devices. More particularly, the present invention pertains to guiding a medical device within a patient, e.g., self-guiding a medical device for treating a patient.

BACKGROUND OF THE INVENTION

Various medical devices are known which can be guided by a user within a patient. For example, guide wires may be manipulated to guide probes, catheters, leads, stents, etc., through various regions of a patient, e.g., arterial or venous pathways. Further, for example, shaped memory alloys may be moved, such as under control of electrical currents, and guided by a user to specific regions within a patient.

Various systems have been described which provide information to a user for use in guiding such medical devices. For example, cameras operating in a visible range, ultrasound techniques, fluoroscopy, magnetic resonance imaging (MRI), and positron emission tomography (PET), have all been proposed for use in guidance systems. For example, one fluoroscopy guidance system includes the observation of two flat real-time x-ray images acquired from different angles. Further, for example, in optical coherence tomography (OCT), a beam of light carried by an optical fiber may illuminate an area within the patient, e.g., the interior of an artery. In a radar-like manner, light reflected back into the fiber from features inside the artery is correlated with the emitted light to capture the depth as well as the angular separation of those features. The features are displayed graphically in two or three dimensions through the use of a suitably programmed computer. A user can then manually guide a working element through the patient with the benefit of the optical images obtained.

However, such systems are generally very large, complex and require expensive visualization techniques. Further, such systems generally do not have the ability to provide desired information with regard to local areas within the patient. For example, optical imaging may give a very efficient and effective physical structure for the region in which a medical device is being guided by the user. However, it is generally not adequate for making distinctions between local areas within the region in which the medical device is guided. For example, optical images may not be adequate to show where the coronary sinus is within the heart; may not be able to provide adequate identification of early atherosclerosis or calcified tissue within the patient; may not be able to be used to identify particular substances within the region; etc. Generally, such optical imaging is only adequate for providing physical structure of the region in which the medical device is being guided by the user. Furthermore, such imaging systems and devices require an external reference point and/or a user, such as a medical technician, to guide the devices.

SUMMARY OF THE INVENTION

The present invention utilizes imaging in the guidance of medical devices such as, for example, cardiac leads, neural stimulating electrodes, drug delivery catheters, stents, ablation catheters, etc. In one particular embodiment, the imaging (e.g., chemical imaging) is used to identify a target area within a region of a patient. A medical device is guided (e.g., self-guided) based on the detected target area.

A method of guiding a medical device within a patient according to the present invention includes acquiring image data of a view region within a region of the patient. The image data generally includes a plurality of image data pixel elements. Each data pixel element is representative of at least one characteristic of a portion within the view region. A movable element of the medical device is self-guided based on the image data.

In one embodiment of the method, the guiding of the movable element is performed by analyzing the image data to detect a target area within the view region based on the plurality of image data pixel elements. The target area includes one or more image data pixel elements having at least one characteristic that is different from other image data pixel elements representative of other portions within the view region. The movable element of the medical device is then self-guided based on the detected target area.

In one embodiment of the method, the characteristic includes at least one of a chemical, physical, mechanical, electrical, thermal, or physiological characteristic.

Another method of guiding a medical device within a patient according to the present invention includes acquiring chemical image data of a view region within the patient. The chemical image data generally includes a plurality of chemical image data pixel elements. Each data pixel element is representative of at least one chemical characteristic (e.g., at least one chemical composition characteristic and/or at least one chemical structure characteristic) of a portion within the view region. A movable element of the medical device is guided based on the chemical image data (e.g., self-guided without user intervention and/or user guided based on a displayed chemical image).

In one embodiment of the method, the guiding of the movable element is performed by analyzing the chemical image data to detect a target area within the view region based on the plurality of chemical image data pixel elements. The target area includes one or more chemical image data pixel elements having at least one chemical characteristic that is different from other chemical image data pixel elements representative of other portions within the view region. The movable element of the medical device is then guided based on the detected target area.

Further, in various embodiments of the methods above, the acquiring of the image data may include sensing natural detectable properties (e.g., the emission of electromagnetic radiation from the view, region or chemical concentration gradients from the view region), and/or certain detectable properties representative of a characteristic may be caused to be exhibited (e.g., via an excitation source such as visual stimuli or chemical stimuli) and thereafter sensed. For example, detectable properties may include electromagnetic radiation, electrical signal activity, mechanical activity, chemical composition properties, chemical structural properties, chemical release properties, etc.

In another embodiment of the methods, physical structure image data representative of the physical structure of the view region is provided in addition to chemical image data. In this embodiment, the guiding, e.g., self-guiding, of the movable element is performed based on the chemical image data and the physical structure image data.

In another embodiment of the methods, image data for a number of view regions is used to generate stored image data, e.g., for a much larger region. For example, such stored image data for a much larger region may be used for comparison purposes with respect to image data acquired at a later time for such view regions.

A guided medical device system according to the present invention is also described. The medical device system includes a movable element of a medical device and a motion control apparatus operatively connected to control motion of the movable element. At least one sensor is associated with the movable element and is operable to acquire image data of a view region within a patient. The image data includes a plurality of image data pixel elements. Each data pixel element is representative of at least one characteristic of a portion within the view region. A computing apparatus is operatively connected to the at least one sensor to receive image data. The computing apparatus generates an output based on the image data. The movable element is self-guided using the motion control apparatus in response to the output based on the image data.

In one embodiment of the system, the computing apparatus is operable to analyze the image data to detect a target area within the view region based on the image data pixel elements. The target area includes one or more image data pixel elements having at least one characteristic that is different from other image data pixel elements representative of the other portions within the view region. The computing apparatus provides an output to the motion control apparatus based on the detected target area.

Another guided medical device system according to the present invention is also described. The medical device system includes a movable element of a medical device and a motion control apparatus operatively connected to control motion of the movable element. At least one sensor is associated with the movable element and is operable to acquire chemical image data of a view region within a patient. The chemical image data includes a plurality of chemical image data pixel elements. Each data pixel element is representative of at least one chemical characteristic of a portion within the view region. A computing apparatus is operatively connected to the at least one sensor to receive chemical image data. The computing apparatus generates an output based on the chemical image data for use in guiding the movable element, e.g., self-guided without user intervention and/or user guided based on a displayed chemical image.

In one embodiment of the system described above, the computing apparatus is operable to analyze the chemical image data to detect a target area within the view region based on the chemical image data pixel elements. The target area includes one or more chemical image data pixel elements having at least one chemical characteristic that is different from other chemical image data pixel elements representative of the other portions within the view region. The computing apparatus provides an output to the motion control apparatus based on the detected target area.

Further, with regard to the methods and systems described herein, the methods and systems may include delivering treatment to a portion of the view area within the patient, e.g., the detected target area. For example, the treatment may be delivered by one of a cardiac lead, a stimulating electrode, a drug delivery catheter, a #tent, an ablation catheter, or any other medical device.

The above summary of the present invention is not intended to describe each embodiment of every implementation of the present invention. Advantages, together with a more complete understanding of the invention, will become apparent and appreciated by referring to the following detailed description and claims taken in conjunction with the accompanying drawings.

DETAILED DESCRIPTION OF THE VARIOUS EMBODIMENTS

Figure 1:
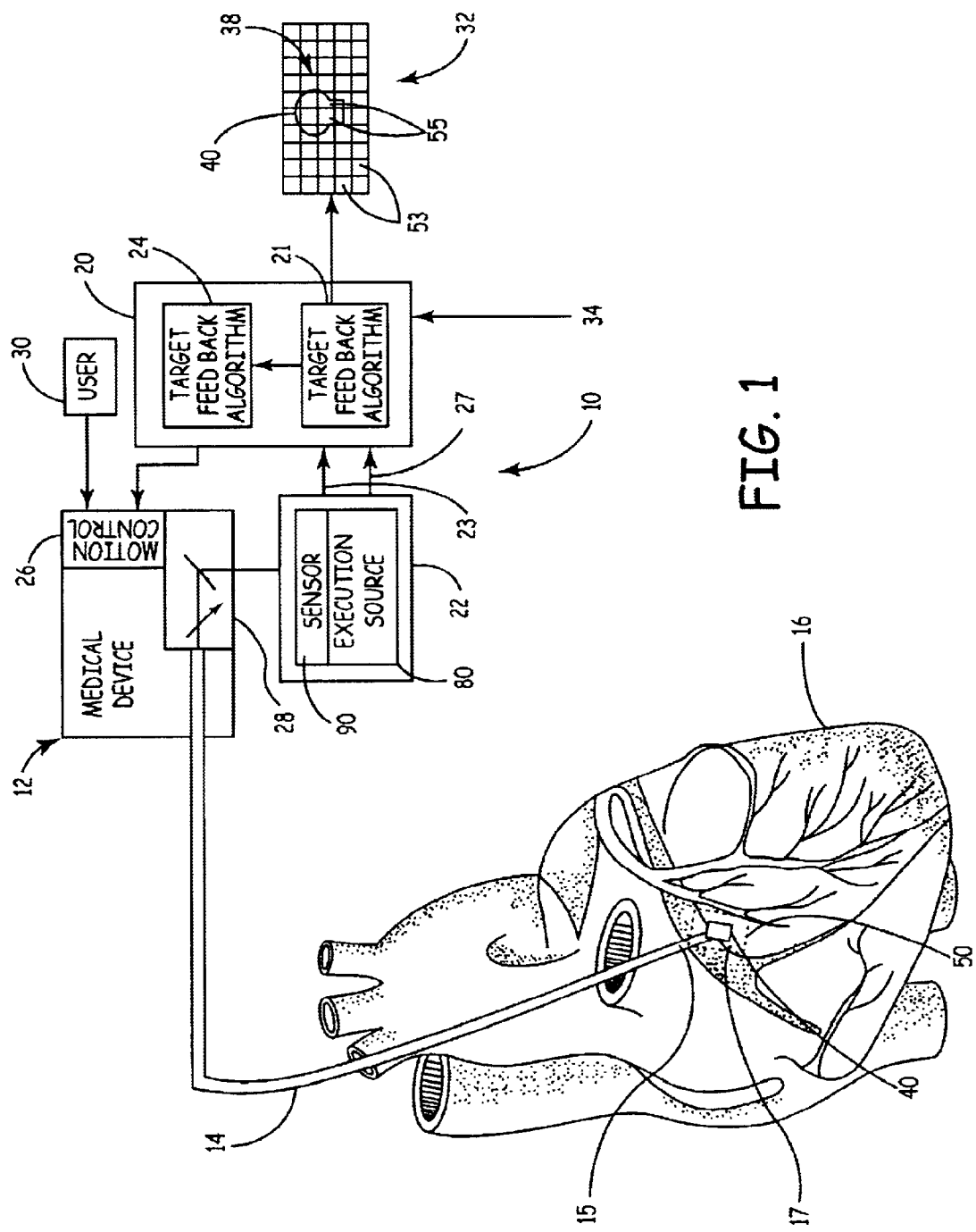
FIG. 1 is a graphical illustration of a guided medical device system according to the present invention.

FIG. 1 shows a guided medical device system according to the present invention which utilizes chemical imaging to guide a medical device to provide for one or more various functions. For example, the system 10 may provide for delivering a particular treatment to a region within a patient (e.g., pharmacological therapy, gene therapy, cancer therapy, ablation), or further, for example, system 10 may provide a map of a particular part or section within a patient, e.g., a portion of the heart 16, a section of an artery or vein, a portion of a brain, etc.

Figure 3:
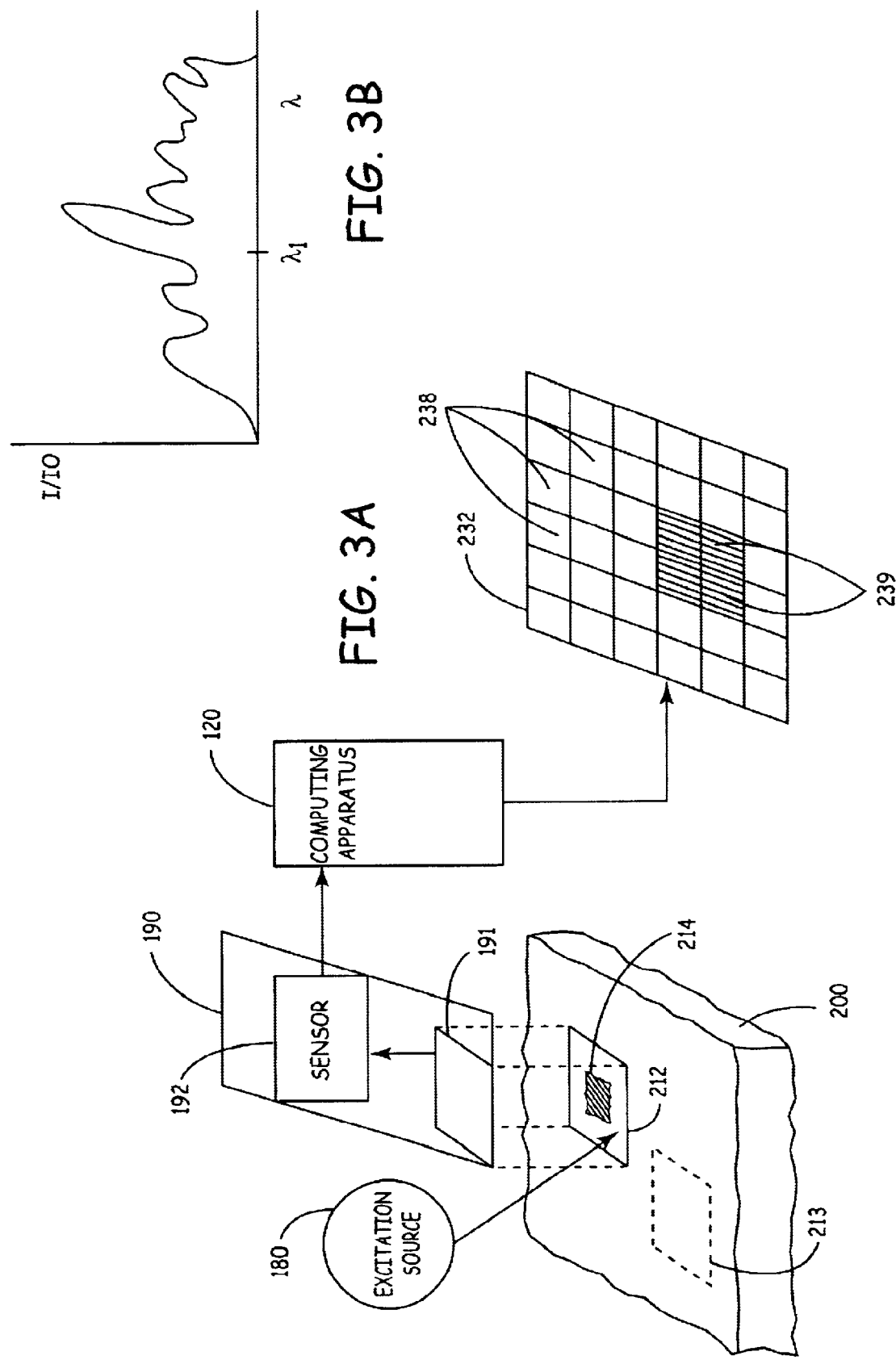
FIGS. 3A and 3B is a block illustration for use in describing chemical imaging as used according to the present invention.
Figure 4:
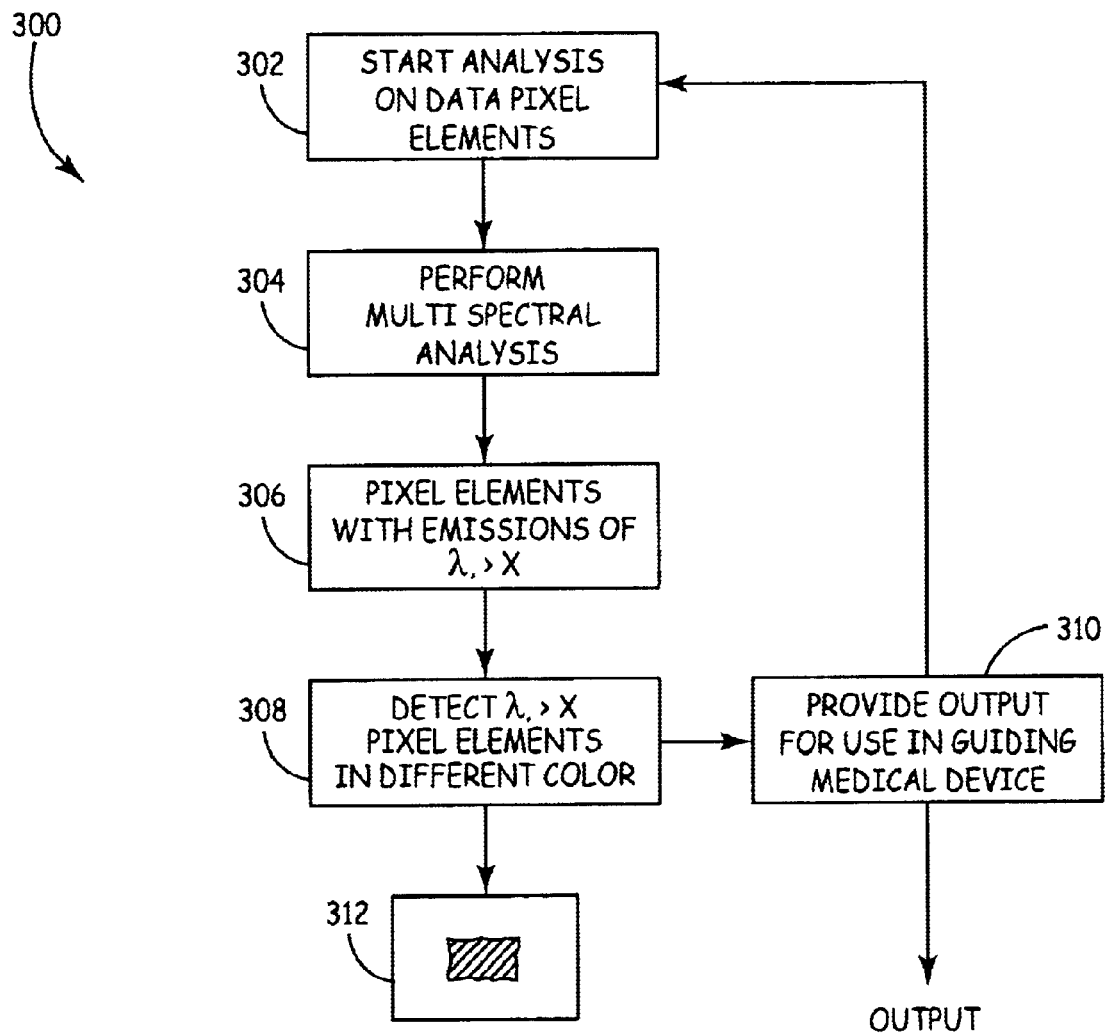
FIG. 4 is a flow diagram of one illustrative chemical imaging and guiding method according to the present invention.
Figure 5:
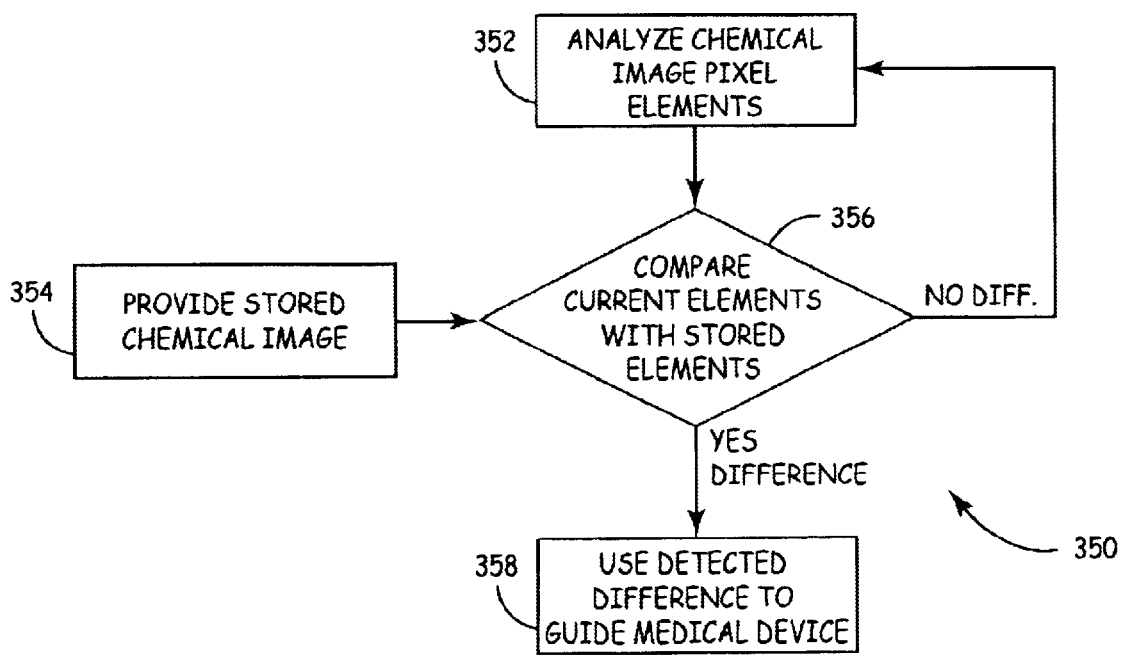
FIG. 5 is one illustrative embodiment of a method of guiding a medical device using chemical imaging according to the present invention.

The guided medical device system 10 as shown in FIG. 1 includes a medical device 12 including a guided element 14, at least one sensor or sensing device 22, and a computing apparatus 20, e.g., microprocessor. According to the present invention, the guided medical device system 10 acquires guiding image data 23 using the medical device 12 and one or more sensing devices 22 of a view region 50 within a patient, e.g., the heart 16 of a patient. Guiding image data includes, but is clearly not limited to, ultraviolet (UV) image data, visible image data, infrared (IR) image data, electrical image data, pressure image data, flow image data, temperature image data, ultrasound image, sound wave image data, magnetic image data, electromagnetic image data, radiation image data, fluoroscopy image data, magnetic resonance imaging (MRI) image data, PET image data, x-ray image data, chemical image data, and/or any other appropriate or suitable type of image data that will provide image information as needed according to the present invention. The description provided below with reference to FIGS. 3–5 is focused on use of chemical image data as defined below. However, any of the types of image data as described above may be used according to the present invention, particularly for self-guided or automatically guided embodiments as described herein.

The guiding image data 23 includes information representative of a plurality of image data pixel elements which are represented in FIG. 1 by the image data pixel elements 38 shown on display 32 which is operatively connected to computing apparatus 20. Each image data pixel element 38 is representative of one or more chemical, physical, mechanical, electrical, thermal, and physiological characteristics of a portion within the view region 50 corresponding to such a pixel element 38. The computing apparatus 20 receives such guiding image data 23 from sensing device 22 and operates on such image data performing one or more application-specific algorithms represented generally by image analysis software 21. The guided element 14 of the medical device 12 is guided based on the image data 23 analyzed by the computing apparatus 20. The image analysis software 21 provides an output which is operated upon by target feedback algorithm 24. Target feedback algorithm 24 provides an output to motion controller 26 of medical device 12 which functions to control movement of guided element 14 of medical device 12. As such, depending upon the result of the image analysis performed by computing apparatus 20, target feedback algorithm 24 provides an output to motion controller 26 to move guided element 14 accordingly.

Generally, according to the present invention, image analysis algorithms 21 are provided for one or more specific applications which involves movement of guided element 14 relative to (e.g., towards or away from) a desired target area 40 within a view region 50. In other words, the distal end 15 of the guided element 14 is moved in a particular direction relative to target area 40 within the view region 50. The image analysis algorithms 21 are used to analyze the image data 23 provided by sensing device 22 to detect a target area 40 within view region 50 based on one or more characteristics represented by the image data pixel elements 38 within the view region 50. The target area 40, as illustratively represented on the display 32, includes one or more image data pixel elements having at least one characteristic that is different from the other image data pixel elements representative of other portions within the view region. In other words, image data pixel elements 55 within the target area 40 have one or more characteristics that are different from the characteristics of image data pixel elements 53 as illustratively represented by the target area 40 shown on the display 32.

Upon operation of the image analysis algorithms 21 upon the image data 23 and detection of a target area 40 within the view region 50, an output can be provided to target feedback algorithm 24 representative of the position of the target area 40 within the view region 50. With such location known, target feedback algorithm 24 provides the appropriate control output to motion controller 26 of medical device 12 for movement of the distal end 15 of guided element 14 to a position as desired relative to the detected target area 40. Upon movement of the distal end 15 of guided element 14 towards the target area 40, or movement of the distal end 15 to any other position as desired upon analysis of the image data 23, image data of an additional view region may be acquired by sensing device 22. Such guiding image data of the additional view region is analyzed, and an output for guiding medical device 12 is provided to target feedback algorithm 24 for provision of a control output to motion controller 26. Such a process is repeatable as desired.

In such a manner, the guided element 14 is self-guided under the closed loop control of image analysis algorithms 21 and target feedback algorithm 24. As used herein, self-guiding refers to the movement of the guided element to a new position under closed loop control, e.g., guiding without user intervention. As such, the medical device system 10 may be considered a self-guided medical device system which provides for guidance of the guided element 14 of medical device 12 to a desired location, e.g., a target area, automatically without user intervention. Preferably, the element 14 is self-guided over a predetermined time period. However, even though self-guided for a particular period of time, a user 30, e.g., a physician, may partially control or assist the movement during other nonself-guided time periods by providing input to motion controller 26. For example, a physician may control the guidance of distal end 15 by viewing a detected target area 40 displayed in the view region 50 represented by the chemical image data pixel elements 38 on an appropriate user viewable display 32. In the alternative, particularly with respect to use of chemical image data, a user 30 may completely control movement of the guided element 14 by providing input to motion controller 26. However, preferably, the system is at least partially self-guided, e.g., positioning of element 14 under control of a user 30 with subsequent self-guiding of the element 14 to one or more other positions.

The guided element 14 of the medical device 12 which can be guided according to the present invention depends upon the application desired and may include one or more different structural elements. In other words, the guided element 14 of medical device 12 may include one or more various available elements that are guided for performance of various functions in any number of applications. For example, the present invention may be used for the guiding of cardiac leads, neural stimulating electrodes, cardiac pacing electrodes, drug delivery catheters, gene delivery catheters, balloon catheters, ablation catheters, anastomotic devices, sutures, staples, vascular clips, adhesives, cannulae, balloon cannulae, guide wires, vascular tubes, membranes, filters, stents, stent delivery elements, endoprostheses, or any other elements or probes used for treatment or for other purposes. Preferably, the guided element 14 includes distal end 15, e.g., element tip. Further, preferably, the guided element 14 includes sensor portion 90 of sensing device 22 for providing information representative of the view region 50. For example, the guided element 14 may include an optical imaging system, a fiber optic probe portion, a polymer-metal lead, a catheter, an endoscope, or even a remotely placed device such as a micro-electro-mechanical (MEM) device. The distal end 15 or element tip could contain a charge coupled device (CCD) chip, voltage probe, pH sensor, chemical sensor, or any other detector for providing the suitable chemical image data for image analysis.

In summary, the guided element 14 may include any sensing portion suitable for providing the chemical imaging data 23. Further, the guided element 14 may include any therapeutic or treatment device (e.g., cardiac leads, ablation devices, or drug delivery devices) or may include elements for providing information for physical structure imaging (e.g., fiber optic elements for optical imaging) in combination with the sensing portion suitable for providing chemical image data 23. However, a sensing element alone may be used depending upon the application, e.g., a chemical imaging application only versus a treatment application. Further, according to the present invention, additional parts of the guided element 14 may be used for providing other functionality such as excitation of the view region 50 as further described below.

Figure 2:
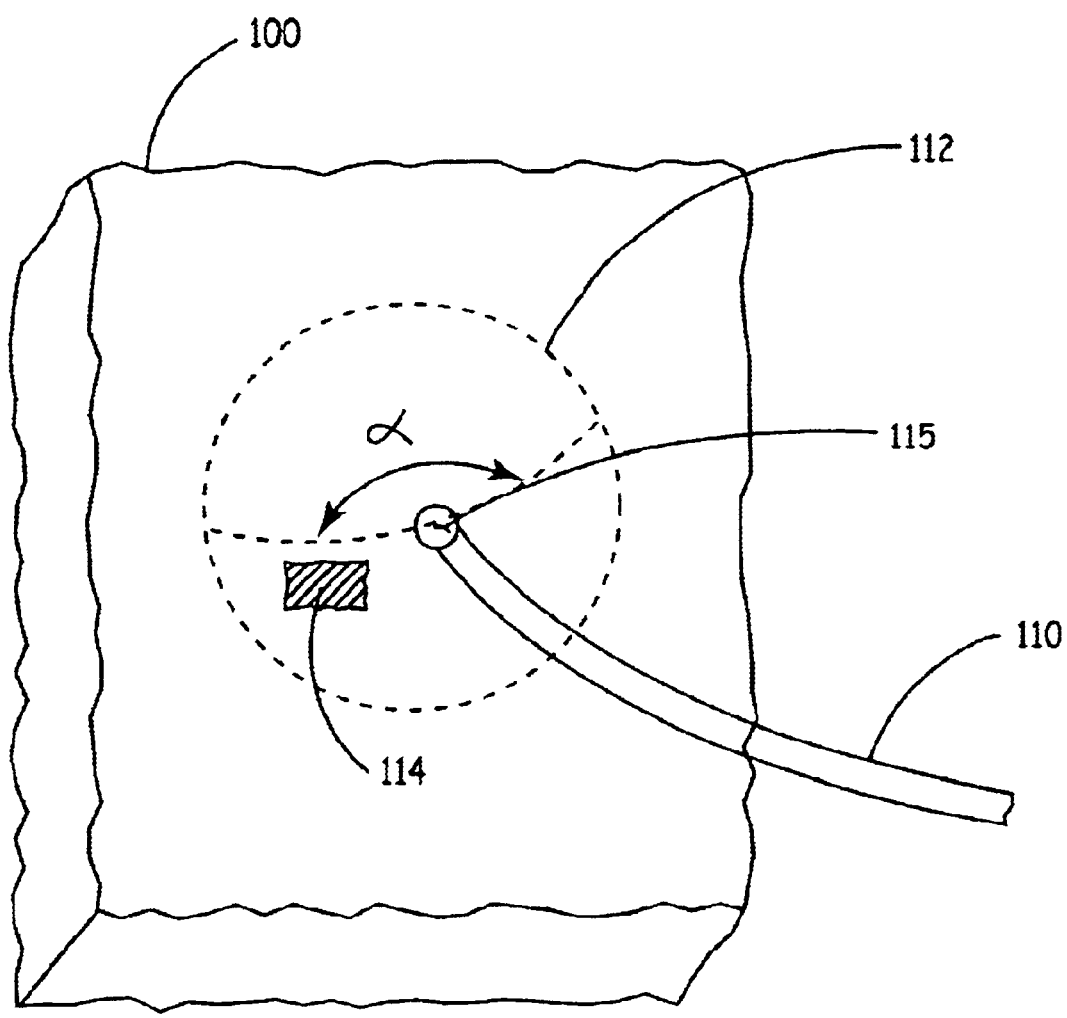
FIG. 2 is one illustrative embodiment of a guided element and a view region for a guided medical device system according to the present invention.

FIG. 2 shows one illustrative embodiment of a guided element 110 including at least a sensing portion at distal end 115 for providing image data for view region 112 of a patient's internal structure 100, e.g., interior of the heart. As shown in FIG. 2, the sensing portion at the distal end 115 has a view angle (α) which dimensionally defines the view region 112. Target area 114 is shown within the view region 112. Preferably, a guided medical device system 10 including guided element 110 guides the element 110 relative to target area 114 as desired for a particular application.

With further reference to FIG. 1, the sensing portion of guided element 14 forms a part of sensing device 22. Sensing device 22 includes sensor 90 which may be interfaced to the sensing portion of guided element 14 via sensing interface 28 (e.g., optical interface, electrical interface, etc.) or may be located at the distal end 15 of the sensor portion of the guided element 14. In other words, the sensing device may be a part of the medical device 12, may be a stand-alone device 22 interfaced through the medical device 12, or may take any other form as necessary to provide chemical image data 23 from the view region 50 to computing apparatus 20.

Further, the sensing device 22 may include an excitation source 80 as further described below depending upon the application of the guided medical device system 10.

The sensor 90 may take the form of any type of sensing device capable of providing guiding image data 23 to computing apparatus 20. For example, the sensor 90 may include one or more camera systems operating in UV, visible, or IR range; electrical sensors; voltage sensors; current sensors; piezoelectric sensors; electromagnetic interference (EMI) sensors; photographic plates; polymer-metal sensors; charge-coupled devices (CCDs); photo diode arrays; micro-chemical sensors (e.g., oxygen sensors, pH sensors, nitric oxide sensors, carbon dioxide sensors, etc.); chemical sensors; pressure sensors; sound wave-sensors; magnetic sensors; UV light sensors; visible light sensors; IR light sensors; radiation sensors; flow sensors; temperature sensors; or to any other appropriate or suitable sensor providing information upon which image analysis algorithm 21 may operate. Such sensors may be used alone or in any combination. For example, with respect to the guiding of a guided element 14 within heart 16, a flow sensor could be used to find regions based on pre-acquired empirical or model flow data within the heart with the use of a voltage probe to locate a more local region that cannot be found using the flow sensor. One such application involves finding the coronary sinus 17 within the heart 16. For example, the coronary sinus may be found by detecting differences in oxygen concentration of blood in the vicinity of a chemical sensor or by detecting lactic acid concentrations via a chemical or electrochemical sensor.

The one or more sensors 90 of sensing device 22 may be used to detect natural detectable properties representative of one or more characteristics, e.g., chemical, physical or physiological, of the view region 50 or may be used to detect properties which are caused to be exhibited within the view region 50. As used herein, natural detectable properties refer to those properties that are detectable in the view region 50 with no external intervention being utilized to cause the occurrence of such properties. For example, natural detectable properties may include the natural emission of electromagnetic radiation (e.g., photons), the natural occurrence of electrical signals (e.g., nodal activity), certain chemical structure of view regions (e.g., crystalline versus non-crystalline areas within the view region), fiber orientation and structure, pH, certain cellular or physiological fluid (e.g., blood or urine) elements (e.g., peptides such as glycopeptides, structural peptides, membrane peptides and cell attachment peptides, proteins such as globular proteins, glycoproteins, enzymes, hormones, growth factors, neurotransmitters, cytokines, platelet agents, inflammatory agents, antibodies, antigens, immunoglobulines, proteoglycans, toxins, polysaccharides, carbohydrates, fatty acids, vitamins, nucleic acids, lectins, ligands, gases, ions), fluid flows (e.g., turbulence or laminar), temperature, pressure, chemical concentration gradients, etc.

Where natural detectable properties are not available to be sensed, such properties may be caused to be exhibited within the view region 50 by an excitation source 80 of the sensing device 22. For example, it is possible to use an excitation source 80 such as, for example, any wavelength of electromagnetic radiation (e.g., visible, fluorescence, infrared (IR), near IR, ultrasound, heat, voltage, current, pH, lasers), cooling source, pressure source, or any other chemical, mechanical, or electrical stimuli source to change chemistry and structure of the molecules within the view region 50 such that chemical image data can be sensed by sensor 90. For example, Raman signals could be detected upon excitation and utilized for analysis.

Further, for example, it may be possible to cause the release of a particular chemical which can be sensed. For example, in the brain, visual stimuli could cause the release of endorphins or other substances in specific areas of the brain. Such endorphins could be used as markers to navigate or guide the guided element 14 through a region.

Further, certain disease areas exhibit characteristic changes in biochemistry and structure. For example, tumors, calcified tissue, cancer cells, damaged organ cells, dopamine, etc., all exhibit detectable chemical characteristics that could be used in detecting a target area 40 within a view region 50 utilizing the present invention.

In one illustrative embodiment herein, the image data 23 is chemical image data representative of one or more chemical characteristics. As used herein, a chemical characteristic being represented in the chemical image data 23 refers the chemical composition of the view region, e.g., the fundamental elements that form the view region, and/or the chemical structure of the view region 50, e.g., crystalline structure, molecular structure, etc. Therefore, chemical characteristic, as used herein, refers to any characteristic representative of a chemical composition and/or structure of the view region.

With respect to the provision of chemical image data to computing apparatus 20, various types of image analysis algorithms 21 may be utilized to analyze the chemical image data. For example, various commercially-available software packages such as NIH Image software available from National Institutes of Health (NIH) and Scion Corporation, Chem Image software available from Chemlcon, Inc., Image-proplus software available from Media Cybernetics, and Metamorph software available from Universal Imaging Corporation, could be utilized to analyze such data. Depending upon the particular application and the target area 40 to be detected, the image analysis algorithms 21 may include various routines for specifically detecting particular target areas. For example, if the target area to be detected is a target area exhibiting a particular wavelength within a spectrum upon excitation, then the image analysis algorithms 21 and any associated routines would be utilized to detect and/or highlight the specific target areas 40 within the view region 50.

In addition to providing chemical image data to computing apparatus 20, the sensor 90 may also provide information with regard to the physical structure of the view region 50. For example, three-dimensional structural data 27 may be optically detected and provided in conjunction with the chemical image data 23 to aid in guiding the guided element 14 within the patient. One skilled in the art will recognize that physical structure data 27 may be created using the same or different sensed data used to create the chemical image data 23. For example, various structural software programs are available to provide such data such as Analyze software available from the Mayo Clinic and Metamorph available from Universal Imaging Corporation. It will be readily recognized that such software may be modified to be adapted into the guided medical device system 10. Three dimensional images can be reconstructed from two dimensional images acquired at various depths. For example, such three dimensional images can be created with the use of confocal microscopy which can be used to reconstruct variable optical planes in the z-axis using x-y information.

Generally, as shown in FIG. 1, once the target area 40 is identified by operation of the image analysis algorithms 21 on the image data 23, e.g., chemical image data or any other guiding image data, an output therefrom is provided such that motion controller 26 may be utilized to guide guided element 14 accordingly. For example, in a self-guided medical device system, the output would be provided to a target adjustment and feedback algorithm 24 to provide appropriate closed loop control of motion controller 26 for correction and tracking of the guided element 14. In other words, much like a "smart bomb" uses a camera to guide a missile or a bomb to a specific target, the targeted area 40 detected through imaging can be used to guide the guided element 14 to the target area 40 within the view region 50.

On the other hand, in addition to control without user intervention, such guiding may be performed through a combination of closed loop control providing correction and tracking of the guided element 14 along with a user 30 providing intervention as necessary, or may be performed solely by a user 30 providing input to a motion controller 26, particularly when the image data is chemical image data, e.g., a display showing a target area 40 within a view region 50 to a user 30 who manually guides the element 14.

The target feedback algorithm 24 and motion controller 26 may take one or more various forms depending upon the application, the type of guided element 14, etc. Generally, in a system where the guided element 14 includes one or more sensing probes, catheters, leads, etc., the motion controller 26 and manner of manipulation may be achieved by guiding wires micro-manipulated by a torque transfer system such as described in U.S. Pat. No. 5,396,902 to Brennen et al., entitled "Steerable Stylet and Manipulative Handle Assembly" issued Mar. 14 1995; U.S. Pat. No. 4,817,613 to Jaraczewski et al., entitled "Guiding Catheter" issued Apr. 4, 1989; U.S. Pat. No. 5,487,757 to Truckai et al., entitled "Multicurve Deflectable Catheter" issued Jan 30, 1996; or by a number of additional techniques. For example, such control of the guided element 14, including the sensing portion for acquiring image data, may include the use of electric or RF signals to control micro-electromechanical devices, or may include use of opto-electric devices. Further, for example, one of the materials used could be a shaped memory alloy moved by electric currents delivered to specific regions such as described in U.S. Pat. No. 5,188,111 to Yates et al., entitled "Device For Seeking an Area of Interest Within a Body" issued Feb. 23, 1993. As such, the present invention is not limited to any particular guided element 14, motion controller 26 or target feedback algorithm 24, as any suitable type of such elements may be used in conjunction with imaging to guide the guided element 14 as desired and in accordance with the present invention.

With reference to FIGS. 3A–3B and FIG. 4, one illustrative embodiment of a method of chemical imaging and guiding a movable medical device 12 according to the present invention shall be described. As shown in FIG. 3A, chemical image data is acquired using sensor 190 and excitation source 180. The chemical image data is a spatial distribution of one or more chemical characteristics of the view region 212 of a region 200 of the patient's body. For example, as described above, the sensor 190 may include sensor elements 191 such as liquid crystal tunable filters (LCTF's), CCD arrays, or other sensors such as described previously herein. The excitation source 180 (which is optionally used if natural detectable properties are not available) causes target area 214 to exhibit at least one different chemical characteristic than the other portions of view region 212. For example, certain biological species such as proteins may fluoresce at specific wavelengths. Other species, for example, may be detectable in a characteristic infrared spectrum. Additionally, many biological and organic compounds are Raman sensitive. Raman analysis is commonly known to one skilled in the art such as described in *Principles of Instrumental* Analysis, D. A. Skoog et al., $4^{th}$ Edition, pp. 69, 296–308 (1992). With the view region 212 and target area 214 exhibiting certain chemical characteristics, sensor elements 191 provide sensed information via sensor interface 192 to computing apparatus 120. The spatial distribution of the chemical characteristics within the view region 212 is used to detect the target area 214 from the remainder of the view region 212 by the computing apparatus 120.

For example, the multi-spectral image acquisition of view region 212 may be performed as represented generally by chemical image data pixel elements 238. Each pixel contains the complete or a large portion of electromagnetic spectrum characteristic of the view region chemistry. The image analysis performed by computing apparatus 120 is used to create maps based on unique chemical characteristics such as absorption and emission properties versus time. For example, as described above, certain biological species such as proteins may fluoresce at specific wavelengths. Such a general chemical characteristic is shown in FIG. 3B. For example, at $\lambda 1$, intensity ($I/I_0$) is shown to be great at this particular wavelength, indicating the characteristic which is to be detected for that particular pixel representative of a portion of the view region 212. For example, as shown in FIG. 3A, pixels 239 are detected to exhibit fluorescence at $\lambda 1$. Therefore, a map of the pixels for view region 212 may be provided with pixels 239 which exhibit fluorescence at $\lambda 1$ being, in some manner, indicated apart from the other pixels which do not exhibit fluorescence at $\lambda 1$, e.g., displayed in a different color.

In this manner, a chemical image is utilized to identify target area 214. The sensor 190 acquired chemical image data in a suitable region of the electromagnetic spectrum. An image analysis algorithm is used to color or otherwise indicate the target area 214 within a map area as shown by display 232 by assigning pixel intensities of specific wavelengths with a particular color. Upon detection of target area 214, an output may be provided to the target feedback algorithm for the guided medical device system such that the guided element may be orientated and tracked automatically or via a special viewer or screen. The guided element associated with the sensor elements 191 can then be manipulated as desired relative to the target area 214.

In other words, computing apparatus 120 may perform an illustrative analysis method 300 as shown in FIG. 4. With the chemical image data acquired, analysis is started on data pixel elements 302. A multi-spectral analysis is performed as shown in block 304. Pixel elements with emission of $\lambda 1 > x$ are detected (block 306). Thereafter, the detected pixel elements which exhibit fluorescence at $\lambda 1 > x$ are provided to be displayed in some readily perceivable form as shown in block 308. An output is provided based on the detected pixel elements for use in guiding the medical device (block 310), and/or a display 312 is provided visually presenting the detected target area 214. Further, analysis may be started again on an additional view region 213 shown in dashed form in FIG. 3A.

One skilled in the art will recognize that any view region may be imaged according to the present invention and that the present invention is not limited to any particular number of view regions to be imaged nor any order of the view regions. For example, the view regions may be adjacent view regions, may be view regions separated by predetermined distances, may be view regions that are more focused in order to more locally detect a detectable target area 214, or may be just used for imaging purposes as further shown in the method 350 of FIG. 5.

As shown in FIG. 5, a chemical image data acquisition method 350 is used for a particular application. The acquired chemical image pixel elements are analyzed as shown in block 352 to be presented in a spatial distribution. Such pixel elements are compared with stored elements as shown in decision block 356. The stored chemical image elements may be provided by any number of sources (block 354). For example, such a stored chemical image may be provided by the guided medical device system 10 as shown in FIG. 1 with a plurality of view regions being mapped and stored by the system. With a comparison of current chemical image data pixel elements to stored previously acquired chemical image data pixel elements, a detectable difference between such elements may result. If a difference between such elements is apparent, such a difference may be used to guide the medical device to further investigate such a difference (block 358). If no difference is apparent, additional view regions may be viewed and compared to additional stored chemical image data. Such a method 350 may be utilized, for example, in diagnosis of certain conditions. For example, if a mapping of chemical image data was performed and a map stored prior to a lesion occurring within a Aft patient, with subsequent imaging of the lesion area being compared to the previously stored chemical data, the target area (i.e., the lesion area) may be detected and used to guide the medical device for treatment of such an area.

This particular comparison method 350 is but one specific illustrative embodiment of a manner of using the present invention. Further, as previously described herein, various types of medical devices for delivering various types of treatments may apply the principles of the above-described invention.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative applications may utilize the imaging and guidance methods and systems as described herein to perform various functions in the medical setting. Various modifications of the illustrative embodiments, as well as additional embodiments of the invention, will be apparent to persons skilled in the art upon reference to this description. For example, the type of sensors and excitation sources and the types of image analysis software and motion control elements will particularly depend upon the application to which the present invention is applied. It is therefore contemplated that the appended claims will cover any such modifications or embodiments that may fall within the scope of the present invention as defined by the accompanying claims.

What is claimed is:

1. A pixel-based imaging system for guiding an elongated medical device extending between a device proximal end and a device distal end during advancement, distal end first, through the body of a patient to locate the device distal end at a target area within a region of the body, the system comprising:
    a movable element proximate to the device distal end that is selecively operable to deflect the device distal end;
    a sensor proximate the device distal end that acquires multi-spectral image data of a view region of the body, the multi-spectral image data comprising chemical image data pixel elements exhibiting a spectrum characteristic of the chemistries of body tissue or fluids within the view region;
    processing means coupled to the sensor for receiving and processing the pixel-based multispectral image data to detect chemical image data pixel elements exhibiting a particular spectral characteristic of a chemical of a target area distinguishable from spectral characteristics of other chemicals of body tissue or fluids within the view region that are not of interest; and
    motion control means coupled to the movable element for operating the movable element to move the device distal end toward the target area, whereby the elongated medical device can be advanced, distal end first, toward the target area, wherein:
        the processing means comprises display means for constructing and displaying the chemical image data pixel elements in a multi color visual image of the view region wherein the chemical image data pixel elements exhibiting the particular spectral characteristic of a chemical of a target area are displayed in an image color signifying the target area to a human operator; and
        the motion control means is operable by the human operator to deflect the device distal end toward the displayed image color to enable advancement of the elongated medical device through the body toward the target area.

2. A pixel-based imaging system for guiding an elongated medical device extending between a device proximal end and a device distal end during advancement, distal end first, through the body of a patient to locate the device distal end at a target area within a region of the body, the system comprising;
    a movable element proximate to the device distal end that is selectively operable to deflect the device distal end;
    a sensor proximate the device distal end that acquires multi-spectral image data of a view region of the body, the multi-spectral image data comprising chemical image data pixel elements exhibiting a spectrum characteristic of the chemistries of body tissue or fluids within the view region;
    processing means coupled to the sensor for receiving and processing the pixel-based multi-spectral image data to detect chemical image data pixel elements exhibiting a particular spectral characteristic of a chemical of a target area distinguishable from spectral characteristics of other chemicals of body tissue or fluids within the view region that are not of interest; and
    motion control means coupled to the movable element for operating the movable element to move the device distal end toward the target area, whereby the elongated medical device can be advanced, distal end first, toward the target area, wherein:
        the processing means comprises display means for constructing and displaying the chemical image data pixel elements in a multicolor visual image of the view region wherein the chemical image data pixel elements exhibiting the particular spectral characteristic of a chemical of a target area are displayed in an image color signifying the target area to a human operator; and
        the motion control means comprises self-guiding means for deflecting the device distal end toward the target area detected from the chemical image data pixel elements exhibiting the particular spectral characteristic of the chemical of the target area within the view region and for advancing the device distal end further through the body toward the target area.

3. A pixel-imaging based medical device system, the system comprising:

an elongated medical device extending between a device proximal end and a device distal end adapted to be advanced, distal end first, through the body of a patient to locate the device distal end at a target area in a region of the body further comprising:
  a movable element proximate to the device distal end that is selectively operable to deflect the device distal end;
  a sensor proximate the device distal end that acquires multi-spectral image data of a view region of the body, the multi-spectral image data comprising chemical image data pixel elements exhibiting a spectrum characteristic of the chemistries of body tissue or fluids within the view region;
  an excitation source proximate the device distal end that causes chemicals of body tissue or fluids of a target area to exhibit a spectral characteristic distinguishable from spectral characteristics of other chemicals in body tissue or fluids within the view region that are not of interest;
  excitation means coupled to the excitation source for causing the excitation source to emit excitation energy to cause chemicals of body tissue or fluids of interest to exhibit the target area spectral characteristic distinguishable from spectral characteristics of chemicals of body tissue or fluids within the view region that are not of interest;
  processing means coupled to the sensor for receiving and processing the image data to detect chemical image data pixel elements exhibiting the target area spectral characteristic; and
  motion control means coupled to the movable element for operating the movable element to move the device distal end toward the target area identified by detected chemical image data pixel elements exhibiting the target area spectral characteristic, whereby the elongated medical device can be advanced, distal end first, toward the targeted region, wherein:
    the processing means comprises display means for constructing and displaying the chemical image data pixel elements in a multi-color visual image of the view region wherein the chemical image data pixel elements exhibiting the particular spectral characteristic of a chemical of a target area are displayed in an image color signifying the target area to a human operator; and
    the motion control means is operable by the human operator to deflect the device distal end toward the displayed image color to enable advancement of the elongated medical device through the body toward the target area.

4. A pixel-imaging based medical device system, the system comprising:
  an elongated medical device extending between a device proximal end and a device distal end adapted to be advanced, distal end first, through the body of a patient to locate the device distal end at a target area in a region of the body further comprising:
    a movable element proximate to the device distal end that is selectively operable to deflect the device distal end;
    a sensor proximate the device distal end that acquires multi-spectral image data of a view region of the body, the multi-spectral image data comprising chemical image data pixel elements exhibiting a spectrum characteristic of the chemistries of body tissue or fluids within the view region;
    an excitation source proximate the device distal end that causes chemicals of body tissue or fluids of a target area to exhibit a spectral characteristic distinguishable from spectral characteristics of other chemicals in body tissue or fluids within the view region that are not of interest;
  excitation means coupled to the excitation source for causing the excitation source to emit excitation energy to cause chemicals of body tissue or fluids of interest to exhibit the target area spectral characteristic distinguishable from spectral characteristics of chemicals of body tissue or fluids within the view region that are not of interest;
  processing means coupled to the sensor for receiving and processing the image data to detect chemical image data pixel elements exhibiting the target area spectral characteristic; and
  motion control means coupled to the movable element for operating the movable element to move the device distal end toward the target area identified by detected chemical image data pixel elements exhibiting the target area spectral characteristic, whereby the elongated medical device can be advanced, distal end first, toward the targeted region, wherein:
    the processing means comprises display means for constructing and displaying the chemical image data pixel elements in a multi-color visual image of the view region wherein the chemical image data pixel elements exhibiting the particular spectral characteristic of a chemical of a target area are displayed in an image color signifying the target area to a human operator; and,
    the motion control means comprises self-guiding means for deflecting the device distal end toward the target area detected from the chemical image data pixel elements exhibiting the particular spectral characteristic of the chemical of the target area within the view region and for advancing the device distal end further through the body toward the target area.

5. A pixel-based method of guiding an elongated medical device extending between a device proximal end and a device distal end through a patient's body to locate the device distal end at a target area within a region of the body, the medical device including:
  a movable element proximate to the device distal end that is selectively operable to deflect the device distal end; and
  a sensor proximate the device distal end that acquires multi-spectral image data of a view region of the body, the multi-spectral image data comprising chemical image data pixel elements exhibiting a spectrum characteristic of the chemistries of body tissue or fluids within the view region including a spectral characteristic of a chemical of the target area distinguishable from the spectral characteristics of other chemicals in body tissue or fluids within the view region that are not of interest,
  the method comprising the steps of:
    advancing the elongated medical device through the patient's body;
    operating the sensor to acquire the multi-spectral image data;
    processing the multi-spectral image data to detect the chemical image data pixel elements exhibiting the target area spectral characteristic; and
    operating the movable element to deflect the device distal end toward the target area indicated by the detected chemical image data pixel elements exhibiting the target area spectral characteristic within the view region, wherein:
   the processing step comprises displaying the chemical image data pixel elements in a multi-color visual image of the view region wherein the chemical image data pixel elements exhibiting the particular spectral characteristic of a chemical of a target area are displayed in an image color signifying the target area to a human operator; and
   the step of operating the movable element comprises deflecting the device distal end toward the displayed Image color signifying the target area to enable advancement of the elongated medical device through the body toward the target area.

6. A pixel-based method of guiding an elongated medical device extending between a device proximal end and a device distal end through a patient's body to locate the device distal end at a target area within a region of the body, the medical device including:
   a movable element proximate to the device distal end that is selectively operable to deflect the device distal end; and
   a sensor proximate the device distal end that acquires multi-spectral image data of a view region of the body, the multi-spectral image data comprising chemical image data pixel elements exhibiting a spectrum characteristic of the chemistries of body tissue or fluids within the view region including a spectral characteristic of a chemical of the target area distinguishable from the spectral characteristics of other chemicals in body tissue or fluids within the view region that are not of interest,
   the method comprising the steps of:
      advancing the elongated medical device through the patient's body;
      operating the sensor to acquire the multi-spectral image data;
      processing the multi-spectral image data to detect the chemical image data pixel elements exhibiting the target area spectral characteristic; and
      operating the movable element to deflect the device distal end toward the target area indicated by the detected chemical image data pixel elements exhibiting the target area spectral characteristic within the view region, wherein:
         the processing step comprises displaying the chemical image data pixel elements in a multi-color visual image of the view region wherein the chemical image data pixel elements exhibiting the particular spectral characteristic of a chemical of a target area are displayed in an image color signifying the target area to a human operator; and
         the step of operating the movable element comprises developing a self-guiding signal applied to the movable element to deflect the device distal end toward the target area detected from the chemical image data pixel elements exhibiting the particular spectral characteristic of the chemical of the target area.

7. A method of guiding an elongated medical device extending between a device proximal end and a device distal end through a patient's body to locate the device distal end at a target area within a region of the body, the medical device including a movable element proximate to the device distal end selectively operable to deflect the device distal end; a sensor proximate the device distal end that acquires multi-spectral image data of a view region of the body, the multi-spectral image data comprising chemical image data pixel elements exhibiting a spectrum characteristic of the chemistries of body tissue or fluids within the view region; and an excitation source proximate the device distal end that causes chemicals of body tissue or fluids of a target area to exhibit a spectral characteristic distinguishable from spectral characteristics of other chemicals in body tissue or fluids within the view region that are not of interest, the method comprising:
   operating the excitation source to emit excitation energy in the view region to cause chemicals of body tissue or fluids of interest to exhibit the target area spectral characteristic distinguishable from spectral characteristics of chemicals of body tissue or fluids within the view region that are not of interest;
   advancing the elongated medical device through the patients body;
   operating the sensor to acquire the multi-spectral image data on a pixel-by-pixel basis;
   processing the multispectral image data on a pixel-by-pixel basis to detect chemical image data pixel elements exhibiting the target area spectral characteristic, and
   operating the movable element to advance the elongated medical device through the patient's body and the device distal end toward the target area indicated by the detected chemical image data pixel elements exhibiting the target area spectral characteristic, wherein:
      the processing step comprises displaying the chemical image data pixel elements in a multi-color visual image of the view region wherein the chemical image data pixel elements exhibiting the particular spectral characteristic of a chemical of a target area are displayed in an image color signifying the target area to a human operator; and
      the step of operating the movable element comprises deflecting the device distal end toward the displayed image color signifying the target area to enable advancement of the elongated medical device through the body toward the target area.

8. A method of guiding an elongated medical device extending between a device proximal end and a device distal end through a patients body to locate the device distal end at a target area within a region of the body, the medical device including a movable element proximate to the device distal end selectively operable to deflect the device distal end; a sensor proximate the device distal end that acquires multi-spectral image data of a view region of the body, the multi-spectral image data comprising chemical image data pixel elements exhibiting a spectrum characteristic of the chemistries of body tissue or fluids within the view region; and an excitation source proximate the device distal end that causes chemicals of body tissue or fluids of a target area to exhibit a spectral characteristic distinguishable from spectral characteristics of other chemicals in body tissue or fluids within the view region that are not of interest,
   the method comprising:
      operating the excitation source to emit excitation energy in the view region to cause chemicals of body tissue or fluids of interest to exhibit the target area spectral characteristic distinguishable from spectral characteristics of chemicals of body tissue or fluids within the view region that are not of interest;
      advancing the elongated medical device through the patient's body:

operating the sensor to acquire the multi-spectral image data on a pixel-by-pixel basis;

processing the multi-spectral image data on a pixel-by-pixel basis to detect chemical image data pixel elements exhibiting the target area spectral characteristic; and operating the movable element to advance the elongated medical device through the patient's body and the device distal end toward the target area indicated by the detected chemical image data pixel elements exhibiting the target area spectral characteristic, wherein:

the processing step comprises displaying the chemical image data pixel elements in a multi-color visual image of the view region wherein the chemical image data pixel elements exhibiting the particular spectral characteristic of a chemical of a target area are displayed in an image color signifying the target area to a human operator; and the step of operating the movable element comprises developing a self-guiding signal applied to the movable element to deflect the device distal end toward the target area detected from the chemical image data pixel elements exhibiting the particular spectral characteristic of the chemical of the target area.

9. A pixel based imaging system for guiding an elongated medical device extending between a device proximal end and a device distal end during advancement distal end first, through the body of a patient to locate the device distal end at a target area within a region of the body, the system comprising:

a movable element proximate to the device distal end that is selectively operable to deflect the device distal end;

a sensor proximate the device distal end that acquires multi-spectral image data of a view region of the body, the multi-spectral image data comprising chemical image data pixel elements exhibiting a spectrum characteristic of the chemistries of body tissue or fluids within the view region;

processing means coupled to the sensor for receiving and processing the pixel-based multi-spectral image data to detect chemical image data pixel elements exhibiting a particular spectral characteristic of a chemical of a target area distinguishable from spectral characteristics of other chemicals of body tissue or fluids within the view region that are not of interest; and motion control means coupled to the movable element for operating the movable element to move the device distal end toward the target area, whereby the elongated medical device can be advanced, distal end first, toward the target area.

10. A pixel-imaging based medical device system, the system comprising:

an elongated medical device extending between a device proximal end and a device distal end adapted to be advanced, distal end first, through the body of a patient to locate the device distal end at a target area in a region of the body further comprising:

a movable element proximate to the device distal end that is selectively operable to deflect the device distal end;

a sensor proximate the device distal end that acquires multi-spectral image data of a view region of the body, the multi-spectral image data comprising chemical image data pixel elements exhibiting a spectrum characteristic of the chemistries of body tissue or fluids within the view region;

an excitation source proximate the device distal end that causes chemicals of body tissue or fluids of a target area to exhibit a spectral characteristic distinguishable from spectral characteristics of other chemicals in body tissue or fluids within the view region that are not of interest;

excitation means coupled to the excitation source for causing the excitation source to emit excitation energy to cause chemicals of body tissue or fluids of interest to exhibit the target area spectral characteristic distinguishable from spectral characteristics of chemicals of body tissue or fluids within the view region that are not of interest;

processing means coupled to the sensor for receiving and processing the image data to detect chemical image data pixel elements exhibiting the target area spectral characteristic; and motion control means coupled to the movable element for operating the movable element to move the device distal end toward the target area identified by detected chemical image data pixel elements exhibiting the target area spectral characteristic, whereby the elongated medical device can be advanced, distal end first, toward the targeted region.

11. A pixel-based method of guiding an elongated medical device extending between a device proximal end and a device distal end through a patient's body to locate the device distal end at a target area within a region of the body, the medical device including:

a movable element proximate to the device distal end that is selectively operable to deflect the device distal end; and a sensor proximate the device distal end that acquires multi-spectral image data of a view region of the body, the multi-spectral image data comprising chemical image data pixel elements exhibiting a spectrum characteristic of the chemistries of body tissue or fluids within the view region including a spectral characteristic of a chemical of the target area distinguishable from the spectral characteristics of other chemicals in body tissue or fluids within the view region that are not of interest, the method comprising the steps of:

advancing the elongated medical device through the patient's body;

operating the sensor to acquire the multi-spectral image data;

processing the multi-spectral image data to detect the chemical image data pixel elements exhibiting the target area spectral characteristic; and operating the movable element to deflect the device distal end toward the target area indicated by the detected chemical image data pixel elements exhibiting the target area spectral characteristic within the view region.

12. A method of guiding an elongated medical device extending between a device proximal end and a device distal end through a patient's body to locate the device distal end at a target area within a region of the body, the medical device including a movable element proximate to the device distal end selectively operable to deflect the device distal end; a sensor proximate the device distal end that acquires multi-spectral image data of a view region of the body, the multi-spectral image data comprising chemical image data pixel elements exhibiting a spectrum characteristic of the chemistries of body tissue or fluids within the view region; and an excitation source proximate the device distal end that causes chemicals of body tissue or fluids of a target area to exhibit a spectral characteristic distinguishable from spectral characteristics of other chemicals in body tissue or fluids within the view region that are not of interest, the method comprising:

operating the excitation source to emit excitation energy in the view region to cause chemicals of body tissue or fluids of interest to exhibit the target area spectral characteristic distinguishable from spectral characteristics of chemicals of body tissue or fluids within the view region that are not of interest;

advancing the elongated medical device through the patient's body;

operating the sensor to acquire the multi-spectral image data on a pixel-by-pixel basis;

processing the multi-spectral image data on a pixel-by-pixel basis to detect chemical image data pixel elements exhibiting the target area spectral characteristic; and operating the movable element to advance the elongated medical device through the patient's body and the device distal end toward the target area indicated by the detected chemical image data pixel elements exhibiting the target area spectral characteristic.

* * * * *

UNITED STATES PATENT AND TRADEMARK OFFICE
CERTIFICATE OF CORRECTION

PATENT NO. : 6,778,846 B1
DATED : August 17, 2004
INVENTOR(S) : Gonzalez Martinez et al.

It is certified that error appears in the above-identified patent and that said Letters Patent is hereby corrected as shown below:

Column 11,
Line 67, delete "multispectral" and insert -- multi-spectral --.

Column 12,
Line 13, delete "multi color" and insert -- multi-color --.

Column 15,
Line 12, delete "Image" and insert -- image --.

Column 16,
Line 21, delete "multispectral" and insert -- multi-spectral --.
Line 45, delete "a patients" and insert -- a patient's --.

Column 17,
Line 29, delete "advancement distal" and insert -- advancement, distal --.

Signed and Sealed this

Seventeenth Day of May, 2005

JON W. DUDAS
*Director of the United States Patent and Trademark Office*